United States Patent [19]
Collazo

[11] Patent Number: 5,954,727
[45] Date of Patent: *Sep. 21, 1999

[54] ACETABULAR CUP POSITIONING TOOL AND METHOD OF POSITIONING AN ACETABULAR CUP

[75] Inventor: Carlos E. Collazo, Ridgefield Park, N.J.

[73] Assignee: Howmedica Inc., New York, N.Y.

[ * ] Notice: This patent is subject to a terminal disclaimer.

[21] Appl. No.: 08/146,277

[22] Filed: Oct. 29, 1993

[51] Int. Cl.$^6$ .................................................. A61B 17/58
[52] U.S. Cl. .............................................. 606/91; 606/99
[58] Field of Search ................................. 606/81, 86, 87, 606/88, 91, 99, 100

[56] References Cited

U.S. PATENT DOCUMENTS

| 3,667,456 | 6/1972 | Charnley | 606/81 |
|---|---|---|---|
| 4,305,394 | 12/1981 | Bertuch | 606/91 |
| 4,662,891 | 5/1987 | Noiles | 606/91 |
| 4,677,972 | 7/1987 | Tornier | 623/22 |
| 5,059,196 | 10/1991 | Coates | 606/99 |
| 5,169,399 | 12/1992 | Ryland | 606/91 |
| 5,171,313 | 12/1992 | Salyer | 606/86 |

Primary Examiner—Michael A. Brown
Attorney, Agent, or Firm—Peter C. Richardson; Lawrence C. Akers; Raymond W. Augustin

[57] ABSTRACT

A positioning tool has an elongated cylindrical section for reversibly engaging an acetabular cup which is insertable through a posterior opening in the cup. The outer diameter of a proximal portion of the cylindrical section is expandable to engage the inner wall of the cup in an interference fit to prevent movement of the cup relative to the tool and hold the cup in engagement with the tool to move the cup with movement of tool to place the cup for implanting at a desired position. The expanded portion of the tool may be contracted to release it from the cup after implantation. The proximal portion, which is attached to the distal portion and separated therefrom by a partial transverse slot, is divided into semi-circular sections by a diametrical vertical slot therebetween. Diametrically opposite quadrants of the proximal portion further contain elongated slots therethrough which are perpendicular to the vertical slot and spaced from the edge of the cylinder by a thin section. The outer diameter of the proximal portion of the cylindrical section may be expanded or contracted by pivoting the semicircular sections around the thin spaces between the elongated slots and edges of the proximal portions. The tool further comprises means for causing the semicircular sections to move relative to each other to expand or contract the diameter of the cylindrical section.

15 Claims, 7 Drawing Sheets

ACETABULAR CUP POSITIONING TOOL AND METHOD OF POSITIONING AN ACETABULAR CUP

BACKGROUND OF THE INVENTION

The present invention relates generally to surgical instruments and, more particularly, to an acetabular cup positioning tool and a method of positioning the acetabular cup using the tool.

Total hip replacement is a surgical reconstructive procedure frequently performed by an orthopedic surgeon. It involves replacement of the acetabulum socket in the pelvis of the patient with an acetabular cup and replacement of the femoral neck on the femur of the patient with a prosthesis that has a ball adapted to engage in the acetabular cup.

In the replacement procedure, the acetabulum socket is reamed out by the surgeon to enlarge it to receive the acetabular cup. The cup in effect will constitute a new socket and lining for the patient's acetabulum. The cup is then inserted in the reamed out recess and maneuvered to the proper angular orientation. Insertion and placement of the cup by the surgeon are carried out either by hand or by use of a hand positioning tool that grips the cup.

The reamed out acetabulum which receives the cup is relatively inaccessible and thus it is difficult for the surgeon to see to maneuver the cup by hand into the proper position after insertion so that the cup can be screwed into place. Insertion and placement of the cup by use of a hand tool is preferred over placement by hand. However, most prior art placement tools are complicated, awkward and difficult to use.

One type of prior art positioning device engages the acetabular cup on the outer periphery thereof. A disadvantage to this type of device is that it obscures the vision of the surgeon in placing the cup, and the fact that it engages the cup on the outer periphery may interfere with full insertion of the cup into the socket. Another type of prior art positioner utilizes a vacuum to hold the cup as it is positioned. However, it is difficult to apply sufficient vacuum to securely hold the cup during positioning. Yet a further prior art device utilizes a screw connection between the positioner tool and the cup, but this limits the direction that the cup can be rotated during insertion and complicates the disengagement of the cup after it has been precisely positioned into the desired location in the socket.

U.S. Pat. No. 5,116,339 describes an acetabular cup positioning tool comprising a head for engaging an acetabular cup, and an elongated member mounting the head adjacent an end that projects from the head and is insertable into an opening through the cup. The member end is expandable for engaging the cup at the opening to prevent movement of the cup relative to the member end and hold the cup in engagement with the head in order to move the cup with movement of the member end to place the cup for implanting at a desired position. The member end also is contractible for releasing the cup after implanting at the desired position.

All of the above prior art devices suffer from the disadvantage that they can only be used in conjunction with acetabular cups, or similar prosthesis, comprising openings at their tops into which the heads of the positioning, or positioning, tools can be inserted.

A need still exists for a positioning tool for use in conjunction with acetabular cups that do not have openings at their tops and may not have any openings.

SUMMARY OF THE INVENTION

The present invention provides an acetabular cup positioning tool and socket replacement system and a method of positioning the acetabular cup designed to satisfy the aforementioned needs. Improvements provided by the positioning tool and system of the present invention enhance the ability of the surgeon to quickly and easily maneuver an inserted acetabular cup, which need not have an anterior opening, so as to place it in the exact position desired, to impact the acetabular cup with sufficient force to seat it at the exact position in which it was placed and to release the tool from the acetabular cup without disturbing its placement and seated position.

The present invention provides a positioning tool for the installation of acetabular cups, and similar devices, which comprises a body consisting of a) a first hollow cylindrical portion;
b) a circular flange abutting the distal end of said cylindrical portion;
c) a second cylindrical portion spaced from said first cylindrical section and attached to the surface thereof by a plurality of thin projections at the periphery thereof;
d) a truncated conical section attached at its first end to the second surface of said second cylindrical portion and having an opening at its second end; and
e) a longitudinal bore through said body wherein
  1) a portion of the bore in the first cylindrical section comprises internal threads to engage the complementary external threads on a turning tool; and
  2) the portion of the bore in the conical section is tapered inwardly from its first to its second end; said portion further comprising a vertical diametrical first slot therethrough which intersects the space between said first and second cylindrical portions and divides the second section into semicircular portions. Each semicircular portion further comprises an elongated second slot therethrough perpendicular to the plane through said first slot and connected thereto the opposite ends of the second slots being spaced from the edge of the cylinder and the longitudinal axis of each slot being spaced from the diametrical axis of the cylinder through the semicircular portions of the second cylindrical section.

The effective diameter of the second cylinder is increased to releasably engage the inner wall of the acetabular cup by a) inserting a first end of an activating tool into the longitudinal bore of the body, wherein said first end is tapered. A portion of the activating tool spaced distally from said first end bears external threads which are complementary to the internal threads of the positioning tool;
b) engaging the complementary threads on the activating tool and first cylindrical portion and turning the activating tool until the tapered end of the spindle enters and moves longitudinally through the tapered hole in the conical portion of the installation head.

As the tapered end of the turning tool moves through the conical portion it forces the two halves thereof apart thereby putting outward pressure on the two halves of the second cylinder causing them to bend backwards around the sections of the second cylinder between the longitudinal slots and the edges of the cylinder. As a result of this motion the opposing edges of the two halves of the cylinder become horizontally spaced from each other and the diameter of the circle circumscribing the resultant cylinder becomes greater than that of the cylinder before the bending backwards of its halves.

Prior to the expansion, the head is inserted into the hollow portion of the acetabular cup within which it will create an interference fit, after the expansion, thereby securely attaching the cup to the head. The acetabular cup is then inserted into the acetabulum socket end by tapping on the end cap of the turning tool after the acetabular cup is seated within the socket. The positioning tool is thereafter released from the acetabular cup by turning the spindle in the reverse direction whereby the tapered end thereof is withdrawn from the head allowing it to return to its normal diameter. The interference fit between the acetabular cup and the head of the positioning tool is thereby destroyed and the tool can be removed from the acetabular cup.

BRIEF DESCRIPTION OF THE DRAWINGS

In the drawings wherein similar reference characters designate like elements throughout the figures.

DETAILED DESCRIPTION OF THE INVENTION

Figure 1A:
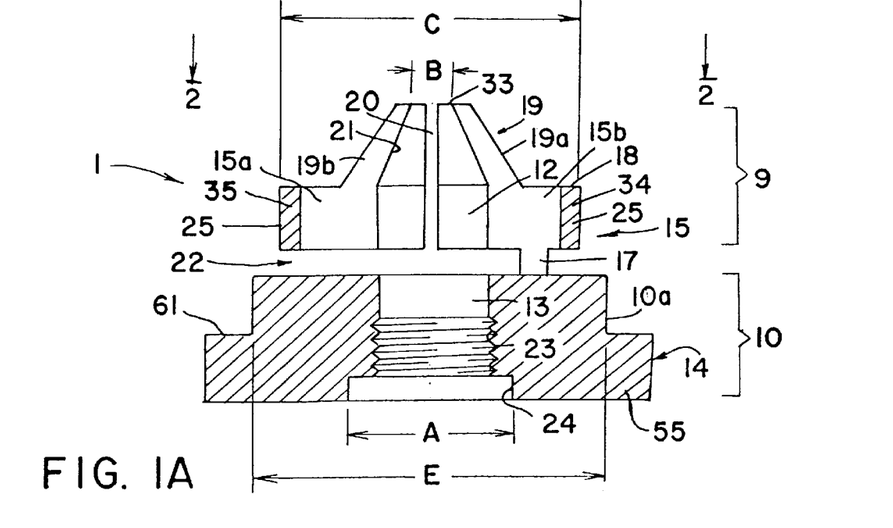
FIG. 1A is a sectional view of one embodiment of the acetabular cup positioning tool of the invention.
Figure 1B:
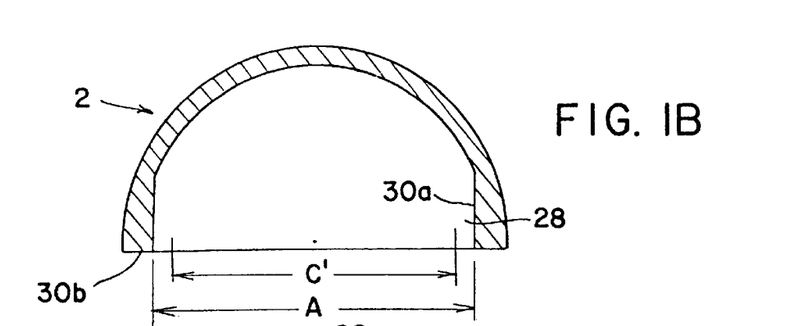
FIG. 1B is a schematic sectional view of an acetabular cup.
Figure 2:
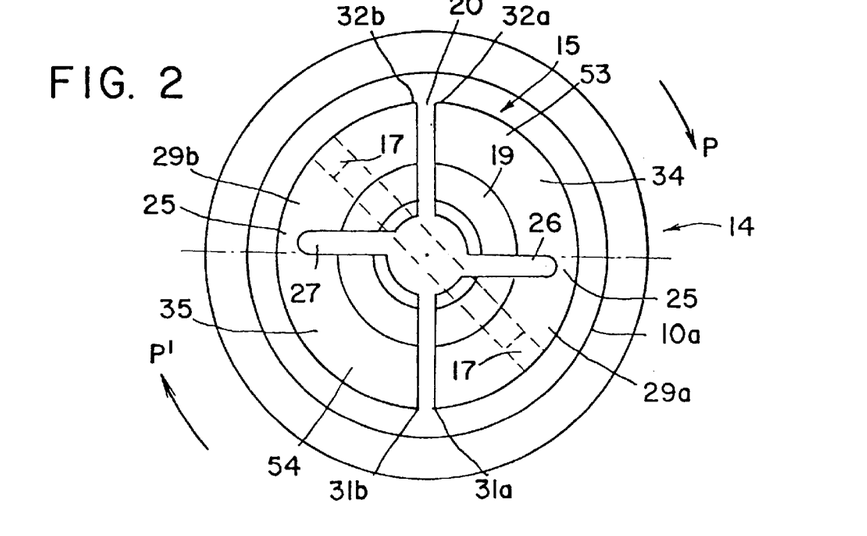
FIG. 2 is a top plan view of the tool of FIG. 1A along line 2—2 of FIG. 1A.

Referring to the drawings, and especially FIGS. 1A and 2, there is shown an acetabular cup positioning tool according to a first embodiment of the invention, designated 1, for implanting and positioning an acetabular cup 2, shown in FIG. 1B, in an acetabulum socket of the pelvis of a patient (not shown).

As can be seen in FIG. 1A, the positioning tool comprises a distal cylindrical first section 14, comprising a cylindrical bore 24, and a cylindrical second section 10a attached thereto comprising a bore 13 comprising internal threads 23, wherein the outer diameter of said first cylindrical section is greater than the outer diameter of the second cylindrical section. A cylindrical third section is spaced from the second surface of the second section 10a by a first slot 22, perpendicular to the longitudinal axis of the positioning tool, and is attached thereto by bridging sections 17. Cylindrical section 15 is terminated on its proximal surface 18 by a truncated conical fourth section 19, spaced from its edges. Section 15 comprises a bore 12 which is connected to and coaxial with bore 13 of second section 10a. Bore 12, in turn, is connected to and coaxial with tapered bore 21 of conical section 19 which comprises a proximal opening 33 having a diameter B.

Sections 15 and 19 further comprise a slot 20 whose plane is perpendicular to the plane of slot 22 between cylinders 10a and 15 and divides section 15 into semicircular sections 34 and 35 and section 19 into semicircular sections 19a and 19b. Sections 34 and 35 comprise longitudinal slots 26 and 27, respectively, which are connected through bore 12 of section 15. The slots 26 and 27, whose longitudinal axes are offset from the diameter of cylinder 15, divide each of semicircular sections 34 and 35 into two quadrants with the slots 26 and 27 being in diametrically opposed quadrants 28a and 29b, respectively.

Figures 6A, 6B, 13:
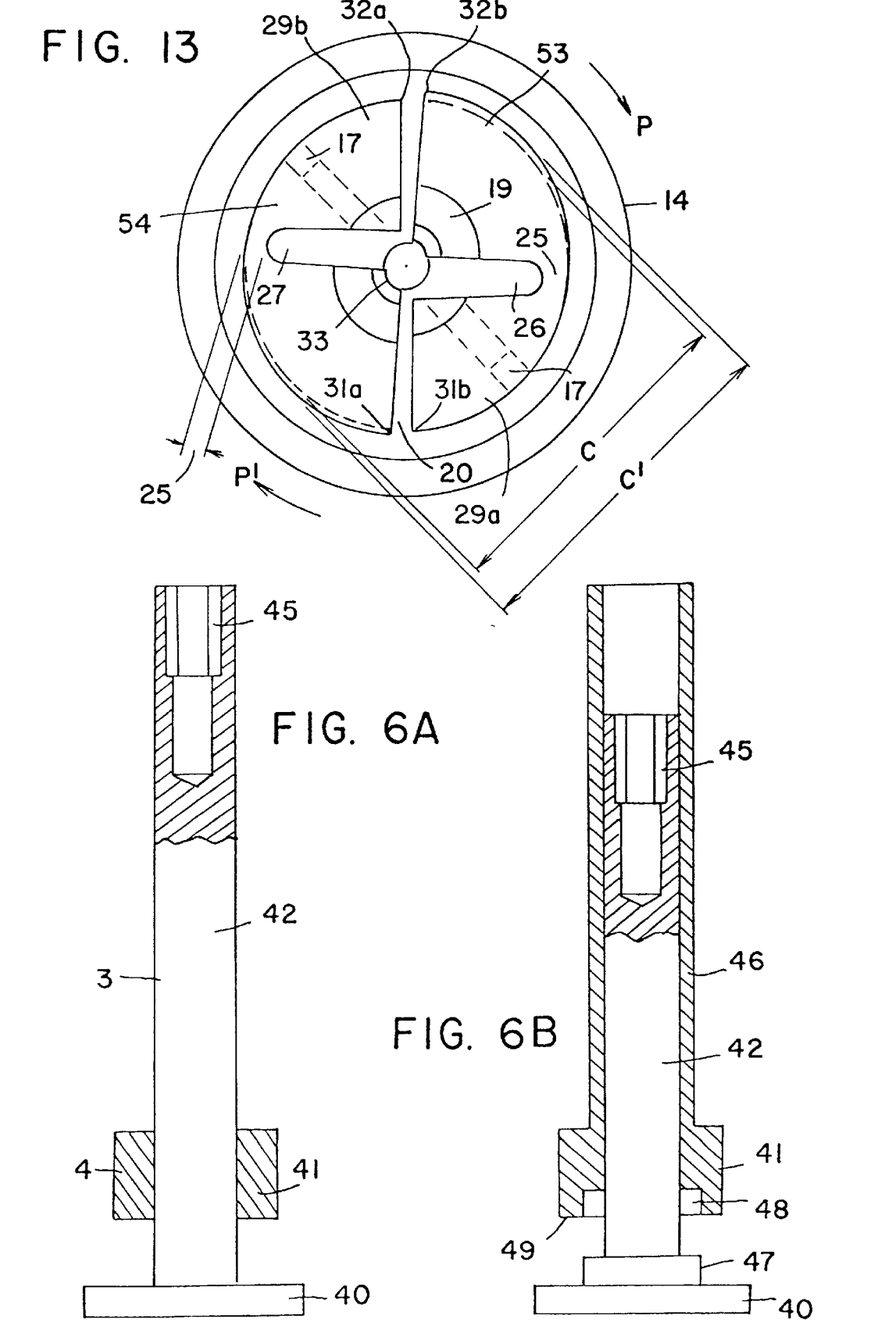
FIG. 6A is a first embodiment of a turning tool for use with the activating tool of FIG. 5.
FIG. 6B is a second embodiment of a turning tool for use with the activating tool of FIG. 6A.
FIG. 13 is top plan view of the acetabular cup positioning and activating tool of FIG. 8 along line 13—13 of FIG. 12.
Figure 7:
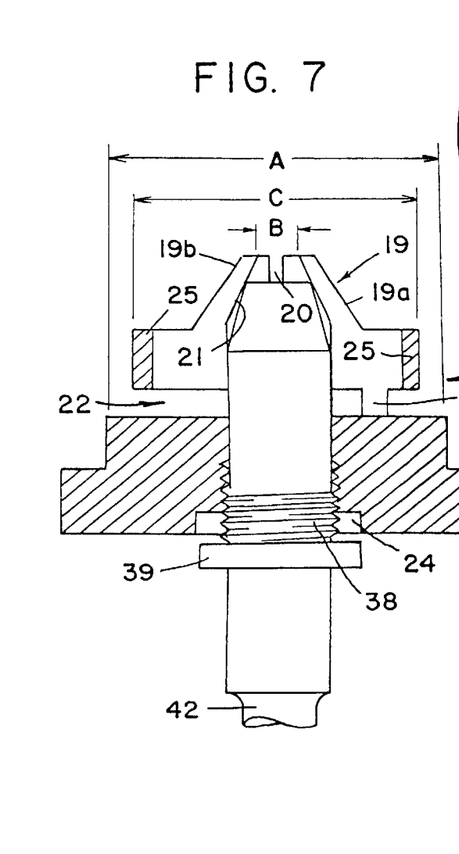
FIG. 7 is a sectional view of the tool of FIG. 1 with the anterior portion of an activating tool partially inserted therein.

In practice, positioning tool 1 is inserted through the posterior opening 28 of an acetabular cup 2, shown in FIG. 1B, until the first surface 61 of first cylindrical section 14 abuts distal surface 30b of acetabular cup 2. The separated portions 19a and 19b of tapered section 19 are forced apart and the diametrically opposed quadrants 53 and 54 of cylinder 15 are caused to bend backwards around their respective sections 25 in the directions of arrows p and p', respectively. As a consequence of said bending backwards the edges 31b and 32a of sections 34 and 35, respectively, are displaced horizontally from their respective opposing edges 31a and 32b. This results in a circumscribed circle for cylinder 15, having a larger diameter C', than in its normal state C, as shown in FIG. 13. The larger effective diameter creates an interference fit between the positioning tool 1 and the acetabular cup 2.

Figures 3, 5:
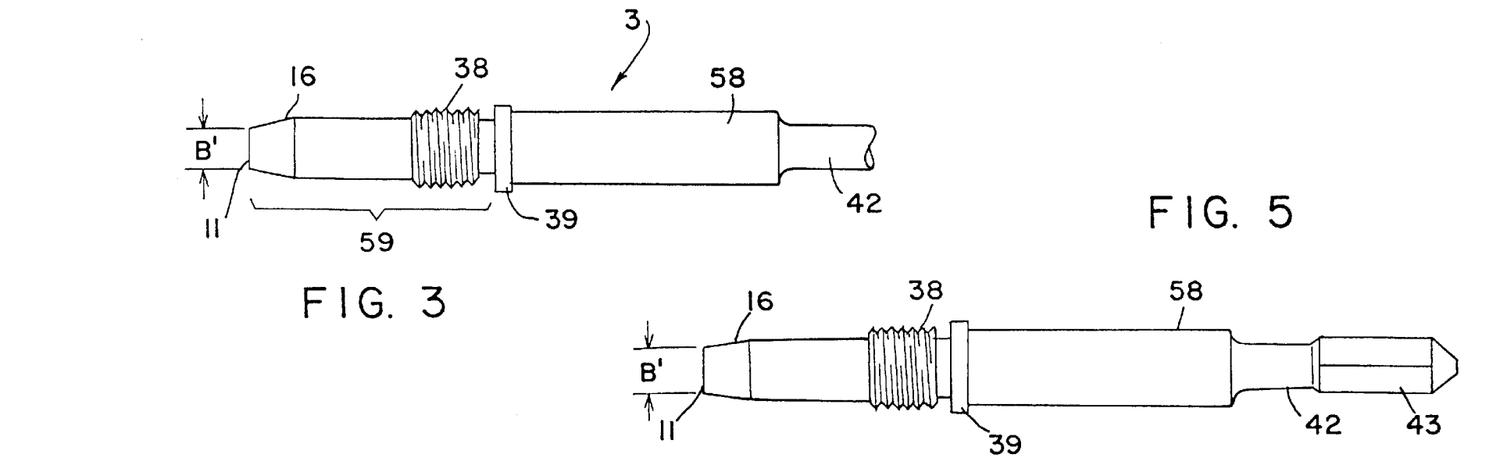
FIG. 3 is an elevational sectional view of the anterior portion of an activating tool for an acetabular cup positioning tool according to the invention.
FIG. 5 is an elevational view of the activating tool of FIG. 2 for use with a separate turning tool.
Figure 4:
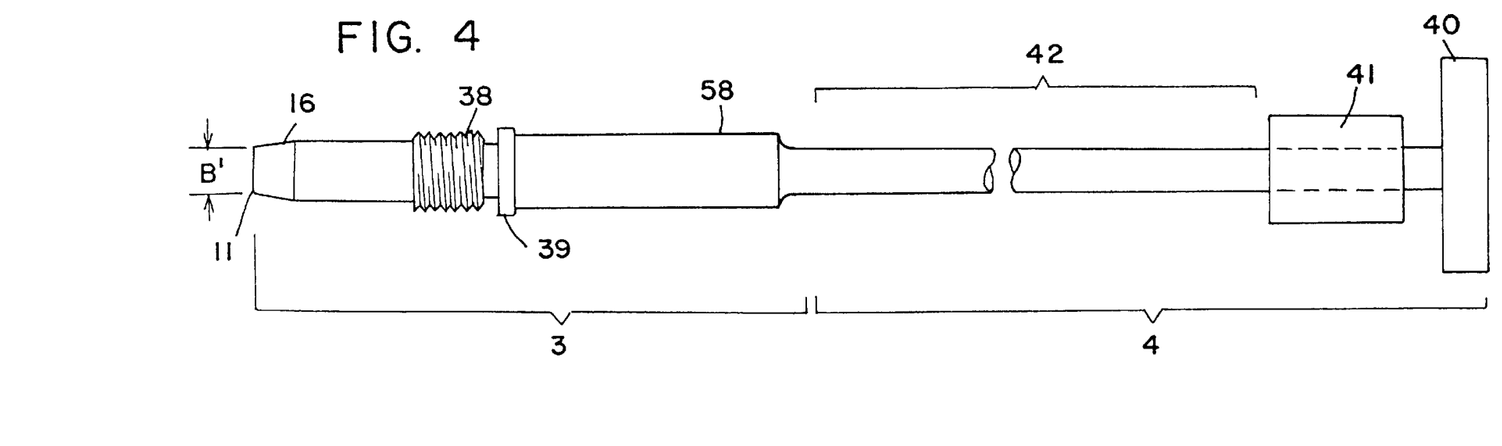
FIG. 4 is an elevational sectional view of an activating tool attached to a turning tool.
Figures 8, 9:
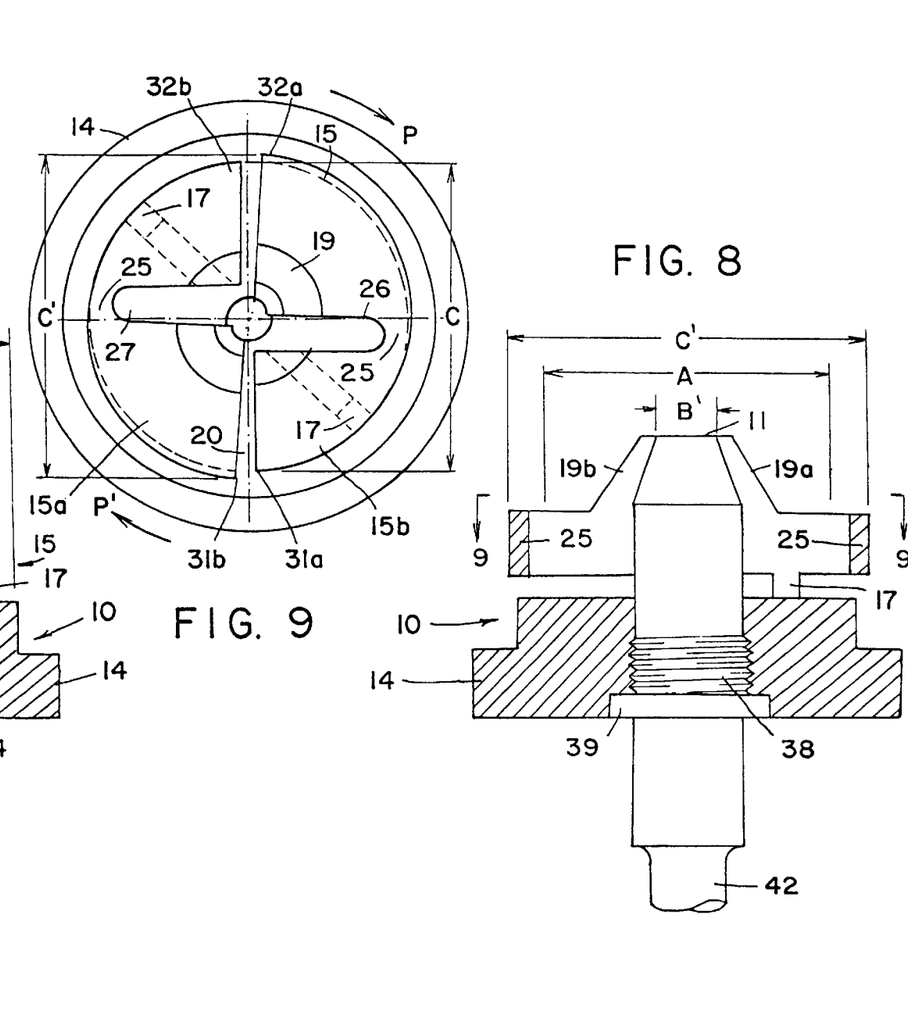
FIG. 8 is a sectional view of the tool of FIG. 1 with the anterior portion of an activating tool completely inserted therein.
FIG. 9 is a top plan view of the acetabular cup positioning and activating tools of FIG. 8 along line 9—9 of FIG. 8.
Figure 10:
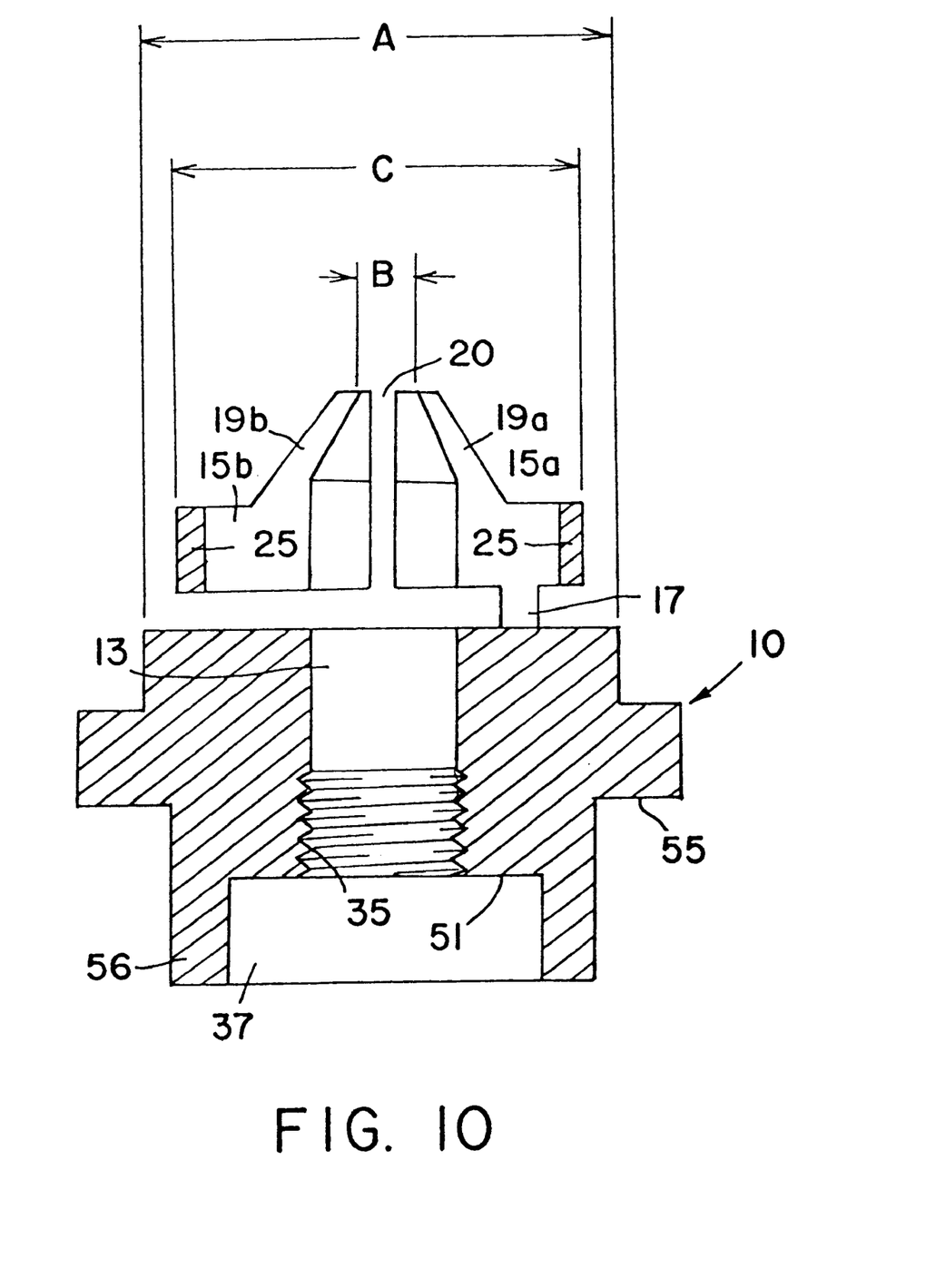
FIG. 10 is a sectional view of a second embodiment of the acetabular cup positioning tool of the invention.
Figure 11:
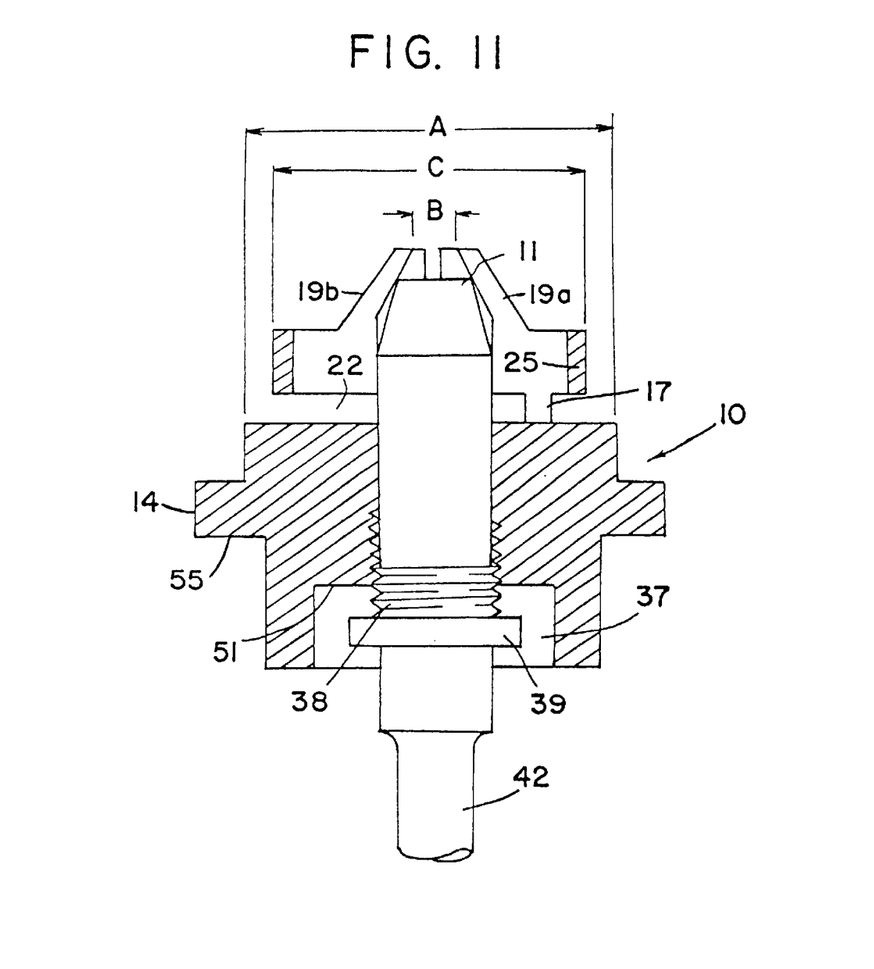
FIG. 11 is a sectional view of the tool of FIG. 10 with the anterior portion of an activating tool partially inserted therein.
Figure 12:
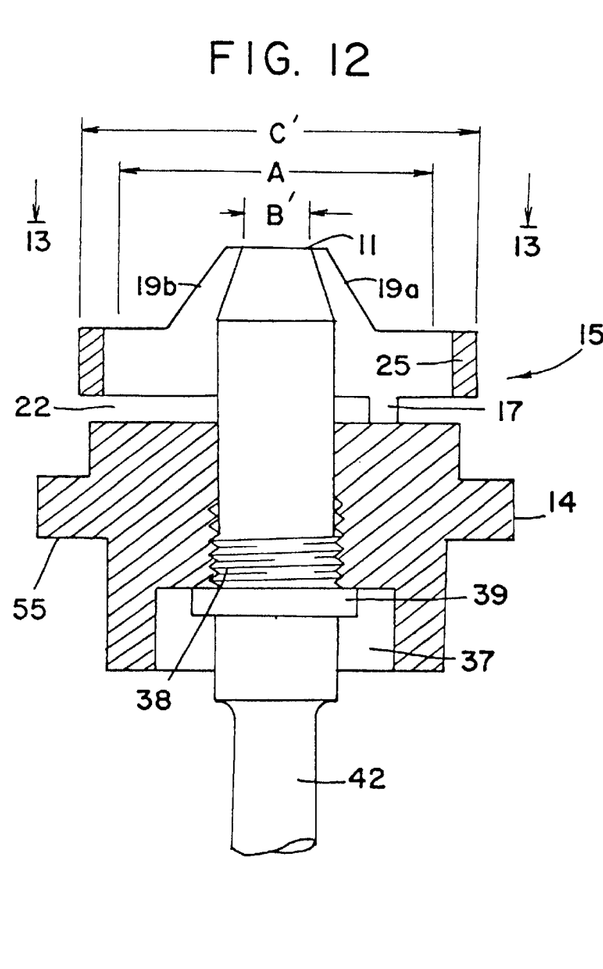
FIG. 12 is a sectional view of the tool of FIG. 10 with the anterior portion of an activating tool completely inserted therein.
Figure 14A:
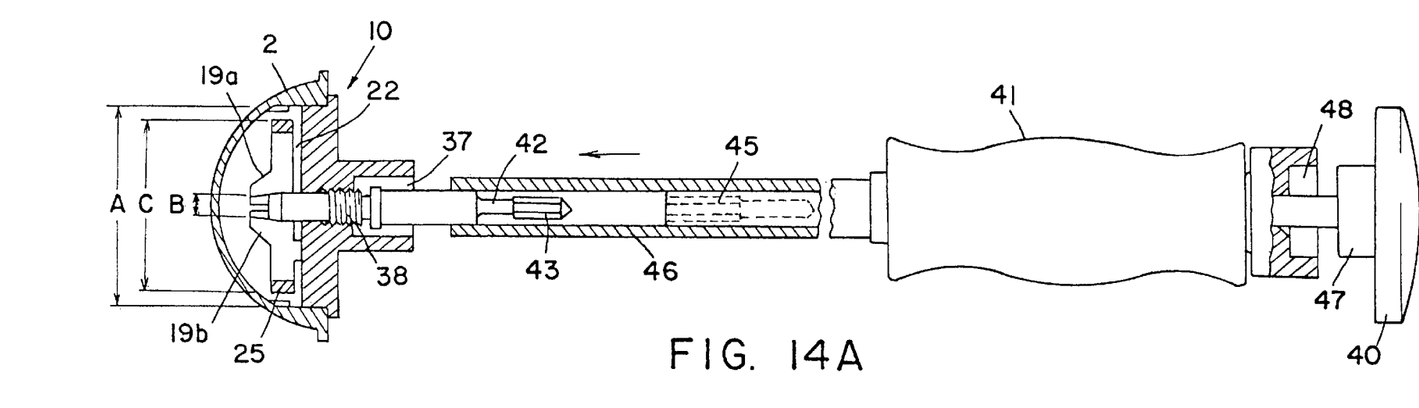
FIG. 14A is a sectional view of the activating, turning and acetabular cup positioning tools and acetabular cup prior to engagement of the acetabular cup positioning tool and acetabular cup.
Figure 14B:
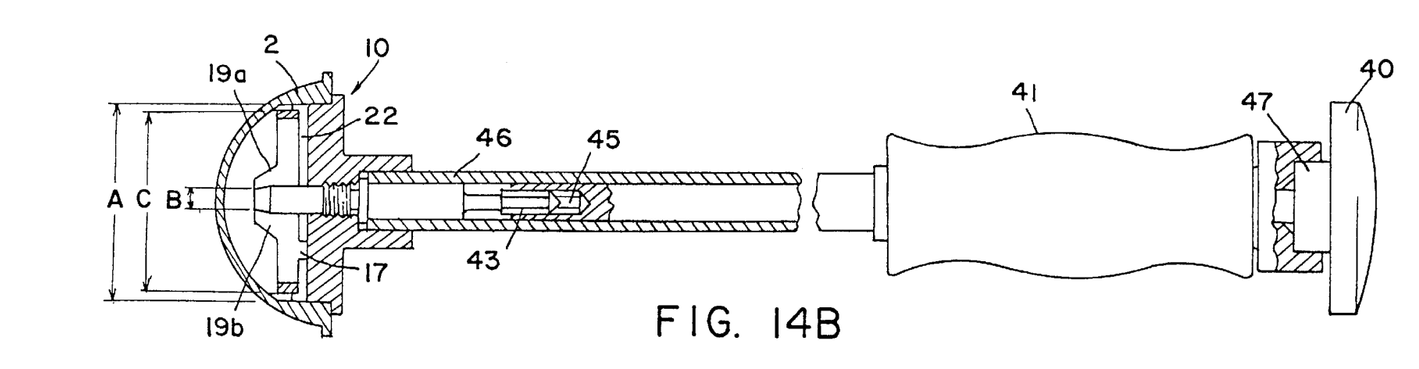
FIG. 14B is a sectional view of the activating, turning and acetabular cup positioning tools and acetabular cup after to engagement of the acetabular cup positioning tool and acetabular cup.

Sections 19a and 19b of tapered section 19 are forced apart by means of an activating tool, designated by the numeral 3, illustrated in FIG. 3. Activating tool 3 comprises a spindle comprising a rod having a first tapered end 16 whose anterior end 11 has an outer diameter B' which is greater than inner diameter B, as shown in FIG. 8, of the anterior opening of conical section 19. A portion of the spindle spaced from said tapered end comprises external threads 38 which are complementary to the internal threads 23 of positioning tool 1. The spindle 3 further comprises a circular flange 39 distally spaced from threads 38 whose outer diameter is greater than the inner diameter of threaded section 13 of the positioning tool 1. As shown in FIG. 4, according to one aspect of this invention, activating tool 3 further comprises handle assembly 4 comprising a longitudinal member 42 terminated at its opposite end by a flat member 40 whose transverse axis is perpendicular to the longitudinal axis of said longitudinal member said flat member being useful as an impaction pad for seating the acetabular cup 2 in the acetabulum socket. The handle assembly further comprises a longitudinal hollow handle 41 spaced proximally from said member 40 which encompasses a portion of said longitudinal member.

Preferably, in a first embodiment of the activating tool of this invention, the spindle 3, and handle assembly 4, as shown in FIGS. 6A and 6B comprise separate parts. Thus, spindle 3, as shown in FIG. 5, comprises a longitudinal portion 43, at its distal end, which has an external hexagonal cross-section. The handle assembly 4, shown in FIG. 6A, in this aspect comprises a longitudinal member 42 containing at its proximal end a longitudinal hole 45 having an internal hexagonal cross-section complementary to, and longer than the second end 43 of spindle 3 of FIG. 5. The handle assembly comprises at its distal end an impact head 40 and handle 41 as described with respect to the aspect of FIG. 4.

In a second embodiment of the activating tool of this invention, the portion of member 42 proximal to handle 41, as shown in FIG. 6B, is surrounded by a hollow tube 46 whose proximal end extends beyond the proximal end of member 42. The rod 42, which is inserted through the distal end of handle 41, is terminated at its second end by an end cap 40. End cap 40 serves as an impaction pad for seating the acetabular cup in the acetabulum socket after it has been properly positioned.

When end cap 40 is turned in one direction, the tapered end of spindle 3 advances longitudinally by means of threaded portion 38, thereof, into threaded portion 23 of the positioning tool, until its forward movement is arrested by interaction of flange 39 with the counter bore 24 of positioning tool 1. Movement of the tapered end 16 of spindle 3 into the tapered hole 21 of conical section 19 causes the sections 19a and 19b hereof, to move apart whereby the respective quadrants 53 and 54, of the second cylindrical section move apart thereby causing the effective diameter of cylinder 15 to expand, from C to C', within the fixed diameter of the acetabular cup 2 thereby creating an interference fit. The interference fit causes secure but releasable engagement between the positioning tool and acetabular cup.

After insertion of the acetabular cup into the acetabulum socket, the end cap is tapped, by means known to the art, thereby causing the acetabular cup to be securely retained within the acetabulum socket. Thereafter, the turning tool is turned in the opposite direction thereby causing spindle 3 to retract longitudinally from the positioning tool 1. When tapered end 16 of spindle 3 has been retracted from conical section 19 of positioning tool 1A, the quadrants 53 and 54 of cylinder 15 and, consequently, its diameter returns to its original position, the interference fit between the positioning tool and acetabular cup no longer exists and the positioning tool can be removed from the acetabular cup.

In a modification of the above embodiment, the counterbore 24 may be eliminated and the forward movement of spindle 3 arrested when the proximal face of flange 39, thereof, contacts the distal face 55 of flange 14 of the positioning tool.

Preparation of the positioning tool of the invention is described, e.g., with reference to the embodiment illustrated in FIG. 1. The tool is constructed from a single piece of stainless steel cylindrical stock.

This tool is formed from said stock by machining a transverse slot 22, therein, spaced from its two ends. The distal end is then machined to form a first distal section 14 and a second section 10a, adjacent thereto, wherein the diameter of the first portion 14 is greater than that of the second section. The proximal portion of the block is machined into a third cylindrical section 15 and a truncated conical section 19. Longitudinal bores 13 and 12 which are connected to each other, through slot 22, and are of equal diameter and coaxial, are machined into second section 10a and third section 15, respectively. Internal threads 23 are machined into bore 13. A bore 24, whose diameter may be equal to or greater than that of bore 13 is formed in first cylindrical section 14. Bore 24 is coaxial with and connected to bore 13. Conical section 19 also comprises a tapered bore 21, which is coaxial with and connected to bore 12 of the third section. After the above mentioned features are machined, cylindrical section 15 is machined in a unique way that enables its outer diameter to be forcefully altered (expanded) with the aid of a threaded spindle such as that illustrated in FIG. 3.

Thus, cylindrical section 15 is machined to create essentially a split washer, thus making its expansion possible. Slot 22 is machined transversely through said cylindrical section. It is, however, not machined entirely through the part. Instead, it is machined from both sides of the part with the purpose of leaving a bridged section 17 allowing sections 10a and 15, adjacent to slot 22, to be connected. A second slot 20a is then machined as shown to intersect with previously machined slot 22. A third slot 20b, coaxial with and connected to slot 20a, is machined into tapered section 19 whereby section 19 becomes a split collet having jaws 19a and 19b. Section 19 further comprises a proximal opening 33. Then slots bores 26 and 27 are machined in the same plane as slot 20 intersecting slot 22. These machining operations result in converting previously mentioned portion 15 into semicircular sections 15a and 15b attached to portion 10 by sections 25. Section 25 functions as the backwards bending points of semicircular sections 15a and 15b to effectively expand cylindrical section 15.

The retraction of semicircular sections 15a and 15b from their expanded positions back to their original relaxed states is made possible by the steel's elastic memory characteristics when properly heat treated.

While several examples of the invention have been described, it is obvious that many changes and modifications may be made thereto without departing from the spirit and scope of the invention.

I claim:

1. A device for positioning an acetabular cup (2), having a distal opening (28) and an inner wall (30), comprising an annular distal portion (30a) and circular distal surface (30b), in an acetabulum socket, said device comprising:
   a longitudinally extending positioning element having a radially expandable plate at one end thereof to releasably engage said cup (2) for positioning and setting in said socket, said radially expanding plate having at least two portions 20, said positioning element further comprising:
   a distal cylindrical first section (14) comprising a bore (52);
   a cylindrical second section (10a), attached to the proximal first surface of the first section (14), comprising internal threads (23) wherein the outer diameter of the first section (14) is greater than the outer diameter of the second section (10a) and the bore (52) of the first section (14) is equal to or greater than the bore (13) of the second section (10a);
   a third section (15) forming said radially expandable plate having a first surface (44) spaced from the first surface (54) of the second section (10a) by a first slot (22) therebetween and attached to said second section (10*a*) by vertical connectors (17) therebetween, said third section (15) having a third bore (12) coaxial with, and an inner diameter equal to the inner diameter of, the second bore (13); a diametrical vertical second slot (20*a*), therethrough, perpendicular to the first slot (22), which divides said section into said two portions (34,35) each portion comprising quadrants (29*a*, 53 and 29*b*, 54, respectively); two elongated vertical slots (26,27), spaced from the vertical edge (57) of third section (15) by a thin portion thereof (25) around which the adjacent quadrant may bend backwards, perpendicular to the planes through second slot (20*a*) and first slot (22), in diametrically opposite quadrants (29*a*, 29*b*) of the semicircular portions (34,35) and spaced from a diametrical plane perpendicular to the planes through, and in connection with, slots (20*a*) and (22);

a truncated conical fourth section (19) rising from the first surface (18) of third section (15) and spaced from the edge (57), having a proximal opening (33) having a diameter of size B, whose bore is tapered inwardly from its distal end to said opening (33) wherein said conical section is being divided into two portions (19*a*, 19*b*) by a vertical diametrical slot (20*b*) coplanar with second slot (20*a*) of third section (15), and the opposing sides (19*a*, 19*b*) of said fourth section (19) can be pushed apart thereby causing diametrically opposed quadrants (53) and (54) to bend backwards around their respective thin portions (25) of third section (15) is increased from (C) to (C') which is equal to the diameters of acetabular cup (2) at its opening (28) and distal portion (30*a*) of its inner wall (30); and an activating element selectively operable to engage said at least two plate portions to cause said radially expanding plate portions to expand, allowing said positioning element to releasably engage the distal portion (30*a*) of the inner wall (30) of the acetabular cup (2), position and set the cup (2) within the socket and thereafter to cause the positioning tool to disengage from the cup (2), said radially expandable plate including a biasing element to cause said at least two portions to release from the inner wall of said cup upon disengagement of said activating element.

2. The device of claim 1 wherein said activating means (3) comprises an elongated member (59), whose outer diameter is about equal to the inner diameter of second bore (13) of positioning tool (1), comprising
i) at one end, a tapered head (16) terminated by a flat surface (11) whose having a diameter of size B'which is greater than the size of proximal opening (33) of the conical section (19) of the cup positioning body (1) before its jaws (19*a*,19*b*) have been pushed apart;
ii) external threads (38), spaced from said tapered head (16), complementary to the internal threads (23) of said cup positioning body (1);
iii) a circular first flange (39), distal from said threads (38), whose outer diameter is greater than the outer diameter of the bore (13) of the cylindrical first section (10) of the positioning tool (1);
iv) connector means (58) to attach the opposite side of the first flange (39) to turning means;
v) turning means comprising a second end to connect to the second end of, and turn, said activating means (3) to cause the head (16) to enter the bore (21) of the fourth section (19) to separate the jaws (19*a*, 19*b*) thereof and cause the effective diameter (C) of the third section (15) to increase and releasably engage the distal portion (30*a*) of inner wall (30) of the acetabular cup (2); and
vi) impact means (40) connected to the distal end of connector means (42) to set the acetabular cup (2) in the acetabulum socket.

3. The device of claim 1 wherein said activating means comprises a unitary article comprising:
a) an activating tool (3);
b) a handle (41); and
c) an impact platform (40).

4. The device of claim 1 wherein said activating means comprises:
a) a first part (3') comprising at its proximal end a tapered head (16') having a proximal flat surface (11'), external threads (38') spaced from said tapered head (16') and a circular flange (39'); and at its opposite end a longitudinal section (43) having a hexagonal cross-section; and
b) a second part comprising an elongated member (42') having at its distal end said impact cap (40') and, a handle (41'), there around, spaced from said distal end and at its proximal end a hexagonal hole (45) co-axial with, longer than and complementary to the hexagonal end of the longitudinal section (43) of the first part (3').

5. The device of claim 4 wherein said second part comprises an elongated rod member (42') comprising said hexagonal hole (45), and said impact cap (40') and said handle (41'), which is spaced proximally from said impact cap (40') which is attached to said rod.

6. The device of claim 5 wherein said rod (42*a*) is reciprocally movable in said handle (41*a*) and is encompassed proximally to said handle by a tube (46) whose proximal end extends beyond the proximal end of said rod (42*a*) and is attached to the proximal end of said handle, said impact cap (40*a*) optionally comprises on its proximal surface a second flange (47) of lesser outer diameter, wherein the distal end of said handle (41*a*) optionally comprises a counterbore (48) to receive said second flange (47) the inner diameter of said counterbore (48) being approximately equal to the outer diameter of said flange (47).

7. The device of claim 6 wherein the internal threads (23) are in all or a portion of bore (13) of second section (10*a*).

8. The device of claim 1 wherein the bore (52) of first section (14) of said positioning tool (1) further comprises a distal portion comprising a large bore (24), having an inner diameter approximately equal to the outer diameter at flange (39), comprising a flat proximal surface (60) which will abut the proximal surface (39) of the activating tool (3) when the activating tool (3) has moved within the positioning tool (1) until the surface (11) of its tapered head (16) reaches the opening (33) of the fourth section (19) of the tool (1).

9. A method of implanting an acetabular cup (2) comprising a posterior opening (28) and an inner wall (30), comprising a distal portion (30*a*) and end surface (30*b*), in an acetabulum socket of a patient which comprises the steps of:
a) inserting through the posterior opening (28) of said acetabular cup (2) a positioning means (1), until the circular surface (30*b*) of cup (2) abuts the first surface (61) of the first section (14) of said positioning means (1) wherein said positioning means (1) comprises an acetabular cup positioning tool (1), adapted for releasably engaging the cup (2) at a distal portion (30*a*) of the inner wall (30) thereof wherein said tool (1) comprises:

1) a distal cylindrical first section (14) comprising a bore (52);
2) a cylindrical second section (10*a*), attached to the proximal first surface of the first section (14), comprising internal threads (23) wherein the outer diameter of the first section (14) is greater than the outer diameter of the second section (10*a*) and the bore (52) of the first section (14) is equal to or greater than the bore (13) of the second section (10*a*);
3) a cylindrical third section (15) whose first surface (44) is spaced from the first surface (54) of the second section (10*a*) by a first slot (22) therebetween and attached to said second section (10*a*) by vertical connectors (17) therebetween, said third section (15) having a third bore (12) coaxial with, and an inner diameter equal to the inner diameter of, the second bore (13); a diametrical vertical second slot (20*a*), therethrough, perpendicular to the first slot (22), which divides said section into semicircular portions (34,35) each comprising quadrants (29*a*, 53 and 29*b*, 54, respectively); two elongated vertical slots (26, 27), spaced from the vertical edge (57) of third section (15) by a thin portion thereof (25) around which the adjacent quadrant may bend backwards, perpendicular to the planes through second slot (20*a*) and first slot (22), in diametrically opposite quadrants (29*a*, 29*b*) of the semicircular portions (34, 35) and spaced from a diametrical plane perpendicular to the planes through, and in connection with, slots (20*a*) and (22);
4) a truncated conical fourth section (19) rising from the first surface (18) of third section (15) and spaced from the edge (57), having a proximal opening (33) having a diameter of size B, whose bore is tapered inwardly from its distal end to said opening (33) wherein said conical section is being divided into two portions (19*a*, 19*b*) by a vertical diametrical slot (20*b*) coplanar with second slot (20*a*) of third section (15), and the opposing sides (19*a*, 19*b*) of said fourth section (19) can be pushed apart thereby causing diametrically opposed quadrants (53) and (54) to bend backwards around their respective thin portions (25) of third section (15) whereby the effective diameter of third section (15) is increased from (C) to (C') which is equal to the diameters of acetabular cup (2) at its opening (28) and distal portion (30*a*) of its inner wall (30);
b) inserting through the bore of the first and second cylindrical sections (14 and 10*a*) of said tool (1) the tapered head (16) of the activating means (3) until the external threads (38) thereof engage the internal threads (23) of the second section (10*a*) of the positioning tool (1); and;
c) turning the activating means (3) until the proximal end (11) of the tapered head (16) thereof reaches the proximal opening (33) of the conical fourth section (19) of the positioning tool (1), whereby the jaws of said fourth section move apart causing the size of the opening (33) of the fourth section (19) to increase from B to B'and diametrically opposing quadrants (53, 54) of the third section (15) to bend backwards around the adjacent thin sections (25) of the third section (15) of the positioning tool (1) in the directions shown by arrows P and P', respectively, thereby causing the effective diameter of the circle circumscribed around said third section (15) to increase until the third section (15) of the positioning tool (1) and the acetabular cup (2) are interferentially locked together;

d) inserting the positioning tool (1) and acetabular cup (2) into the acetabulum socket and positioning acetabular cup (2) therein;
e) tapping the impact end (40) of the activating means to seat the acetabular cup (2) in the acetabulum socket; and
f) turning the handle (40) of the activating means (3) in the direction opposite to that of step c until the external thread thereof disengages from the internal thread of the positioning tool and the activating tool is withdrawn therefrom thereby permitting the displaced quadrants of the second cylindrical section threads (38) thereof disengage from the internal threads (23) of the positioning tool (1) and the head (16) of activating means (3) is withdrawn from the fourth section (19) and the jaws (19*a*, 19*b*) thereof and, consequently, the displaced quadrants of the third section (15) of the positioning tool (1) are permitted to return to their normal positions whereby the diameter of the circumscribed circle around said third section (15) is decreased thereby allowing the positioning tool (1) to be withdrawn from the acetabular cup (2).

10. The method of claim 9 wherein the activating means comprises an elongated member (59), whose outer diameter is about equal to the inner diameter of second bore (13) of positioning tool (1), comprising;
a) at one end a tapered head (16) whose proximal outer diameter (B') is greater than the inner diameter at the opening (33) of the conical section (19) of the positioning tool (1);
b) external threads (38), spaced from said tapered head (16), complementary to the internal threads (23) of positioning tool (1);
c) a circular flange (39) whose outer diameter is greater than the inner diameter of the bore (13) of the second section (10*a*) of the positioning tool (1);
d) means (42) to attach the opposite side of the flange (39) to a first end of handle means; and
e) impact cap means (40) attached to the opposite end of said handle means.

11. The method of claim 9 wherein the activating means comprise a unitary article.

12. The method of claim 9 wherein the activating means comprises;
i) at one end, a tapered head (16) terminated by a flat surface (11) having a diameter of size B' which is greater than the size of proximal opening (33) of the conical section (19) of the cup positioning body (1) before its jaws (19*a*, 19*b*) have been spread;
ii) external threads (38), spaced from said head (16), complementary to the internal threads (23) of said cup positioning body (1);
iii) a circular first flange (39), distal from said threads (38), whose outer diameter is greater than the outer diameter of the bore (13) of the cylindrical first section (10) of the positioning tool (1); and
iv) connector means (58) to attach the opposite side of the first flange (39) to turning means;
v) turning means comprising, handle means comprising a second end to connect to the second end of, and turn, said activating means (3) to cause the activating tool (3) to enter the fourth section (19) and separate the jaws (19*a*, 19*b*) thereby causing the effective diameter (C) of said third section (15) to increase and releasably engage the distal portion (30*a*) of inner wall (30) of the acetabular cup (2) and;

vi) impact means (40), connected to the distal end of connector means (42), to set the acetabular cup (2) in the acetabulum socket.

13. The method of claim 12 wherein said second part comprises a longitudinal rod (42') and said hexagonal hole (45) and said handle (41) are attached to said rod.

14. The method of claim 13 wherein said rod (42a) is reciprocally movable in said handle (41a) and is encompassed proximally to said handle by a tube (46) whose proximal end extends beyond the proximal end of said rod and is attached to the proximal end of said handle (41a), said impact cap (40a) optionally comprises on its proximal surface a second flange (47) of lesser outer diameter, wherein the distal end of said handle optionally comprises a counterbore (48) to receive said second flange (47) the inner diameter of said counterbore (48) being approximately equal to the outer diameter of said flange (47).

15. The method of claim 9 wherein said positioning tool (1) further comprises a distal bore (24), in said first section (14) comprising a flat anterior surface (60) which will abut the proximal surface of the flange (39) when the proximal surface (11) of head (16) of the activating tool (3) has reached the opening (33) of the positioning tool (1).

\* \* \* \* \*

UNITED STATES PATENT AND TRADEMARK OFFICE
CERTIFICATE OF CORRECTION

PATENT NO. : 5,954,727
DATED : September 21, 1999
INVENTOR(S) : Collazo

It is certified that error appears in the above-identified patent and that said Letters Patent is hereby corrected as shown below:

Column 3,
Line 60, cancel "to".

Column 4,
Line 66, after "member", insert --,--.

Column 7,
Line 30, "is" should read -- and --.
Line 45, "means" should read -- element --.
Line 50, cancel the word "whose".
Line 65, "means" should read -- element --.

Column 8,
Lines 8 and 13, "means" should read -- element --.
Line 46, "the" (second occurrence) should read -- a --.
Line 47, "tool" should read -- element --.
Line 51, "the" (third occurrence) should read -- an --.

Column 10,
Line 13, before "disengage", insert -- to --.

Column 12,
Line 2, after "(47)", insert -- , --.

Signed and Sealed this

Twentieth Day of May, 2003

JAMES E. ROGAN
*Director of the United States Patent and Trademark Office*